United States Patent
Pillich et al.

(10) Patent No.: US 8,043,624 B2
(45) Date of Patent: Oct. 25, 2011

(54) COMPOSITIONS AND METHODS FOR TREATMENT OF MICROBIAL INFECTIONS

(75) Inventors: Jiri Pillich, Brno (CZ); John C. Balcarek, Huntsville, AL (US)

(73) Assignee: Immunology Laboratories, Inc., Birmingham, AL (US)

( * ) Notice: Subject to any disclaimer, the term of this patent is extended or adjusted under 35 U.S.C. 154(b) by 430 days.

(21) Appl. No.: 11/986,715

(22) Filed: Nov. 26, 2007

(65) Prior Publication Data
US 2010/0003233 A1      Jan. 7, 2010

Related U.S. Application Data

(63) Continuation-in-part of application No. 11/170,972, filed on Jun. 30, 2005, now Pat. No. 7,329,409, which is a continuation of application No. 10/367,213, filed on Feb. 13, 2003, now Pat. No. 6,929,798.

(60) Provisional application No. 60/860,912, filed on Nov. 24, 2006, provisional application No. 60/356,483, filed on Feb. 13, 2002.

(51) Int. Cl.
*A61K 39/02*      (2006.01)

(52) U.S. Cl. ............. 424/243.1; 424/197.11; 424/234.1; 530/350

(58) Field of Classification Search ................. None
See application file for complete search history.

(56) References Cited

U.S. PATENT DOCUMENTS 6,929,798 B2 *   8/2005   Pillich et al. ............... 424/243.1
7,329,409 B2 *   2/2008   Pillich et al. ............... 424/243.1

OTHER PUBLICATIONS

Carneiro et al (Microbes and Infection. 2004. 6: 604-608).*

* cited by examiner

*Primary Examiner* — Jennifer Graser
(74) *Attorney, Agent, or Firm* — Ballard Spahr LLP

(57) ABSTRACT

The present invention relates to methods and compositions for treatment of microbial infections and for the enhancement of resistance to infection. The invention comprises administration of an effective amount of a protein isolated from bacterial lysate compositions for the treatment of pathological conditions of microbial infections. The present invention can also be used to enhance the immune system to prevent infections by the administration of an effective amount of the compositions.

9 Claims, 4 Drawing Sheets

| | |
|---|---|
| FRACTION 1 (70 kDa | |
| 1 | Major Tail Sheath Protein (phage K, 812, G1) |
| 2 | Major Tail Sheath Protein (phage K, 812, G1) |
| 3 | Major Tail Sheath Protein (phage K, 812, G1) |
| | |
| FRACTION 2 (50 kDa | |
| 1 | Capsid protein (phage K) Enolase (*S. aureus*) |
| 2 | Capsid protein (phage K) Enolase (*S. aureus*) |
| 3 | Capsid protein (phage K) Enolase (*S. aureus*) |
| | |
| FRACTION 4 (36 kDa | |
| 1 | f-b aldolase (*S. aureus*) ORF 45 (Phage K) Ptsb lipoprotein (*S. aureus*) ORF57 (phage K) |
| 2 | Ppp phosphatase-frag. (*S. aureus*) Capsid protein frag, (phage K) Elong. Factor Ts (*S. aureus*) Pb baseplate prot (phage K) |
| 3 | ORF 95 (phage K) |
| | |
| FRACTION 5 (30 kDa | |
| 1 | ORF95 (Phage K) 30S ribosomal pro L1 |
| 2 | ABC transporter (*S. aureus*) ORF95 (phage K) ORF055 (Phage G1) |
| 3 | Triosphos. Isomerase (*S. aureus*) |

FIGURE 4

COMPOSITIONS AND METHODS FOR TREATMENT OF MICROBIAL INFECTIONS

RELATED APPLICATIONS

This application claims the benefit of U.S. Provisional Application No. 60/860,912, filed on Nov. 24, 2006, which is incorporated herein in its entirety, and is a continuation-in-part of and claims priority to U.S. patent application No. 11/170,792, now U.S. Pat. No. 7,329,409, filed on Jun. 30, 2005, which is a continuation of U.S. patent application No. 10/367,213, now U.S. Pat. No. 6,929,798, filed on Feb. 13, 2003, which claims the benefit of U.S. Provisional Application No. 60/356,483 filed on Feb. 13, 2002.

FIELD OF THE INVENTION

The present invention relates generally to the treatment of microbial infections. More specifically, the invention relates to methods and compositions for the enhancement of an immune response in a human or animal to microbial infections.

BACKGROUND OF THE INVENTION

The idea of using phages for treatment of infectious diseases was initially proposed by d'Herelle in 1917. In the 1920s, the discovery of bacteriophages was thought to be the answer for treatment of bacterial infections. Bacteriophages invade and destroy bacteria and appeared to be the selective therapeutic bullet that would knock out bacteria invading an animal or plant host. Unfortunately, the phages were not as effective in killing bacteria in host organisms as they were in killing bacteria in vitro. The development of antibiotics in the 1940s as the preferred treatment for bacterial infections led to a decline in research into use of bacteriophages for treatments of infectious diseases.

In a few countries, notably in Eastern Europe and India, research continued in the use of bacteriophages and bacterial lysates for treatment of infectious diseases and enhancement of immune responses. Though much of that research is still not accepted widely in other industrialized countries, a renewed interest in this research is growing as a result of the occurrence of antibiotic resistant bacteria. Many infectious diseases that were once easily treatable with antibiotics are now a serious health threat because the bacteria are resistant to most, if not all, antibiotics. Medical science is searching for treatments that can respond to these resistant bacteria in a way that does not lead to even more resistant infectious strains.

The U.S. Centers for Disease Control and Prevention estimates that 20% to 50% of prescribed antibiotics are unnecessary. The overuse of antibiotics in medicine and agriculture has greatly fostered the development of resistant strains of bacteria. In a microenvironment bombarded with antibiotics, the few bacteria that can resist the drugs proliferate. Bacteria are becoming increasingly resistant to what were previously considered "last resort" antibiotics.

Bacteriophage therapy has not gained much attention or acceptance in most industrialized countries, in part due to the reliance on pharmaceuticals, such as antibiotic treatment for bacterial infections. What is needed are compositions and methods for treatment and prevention of microbial infections that do not rely on pharmaceutical antibiotic therapies. Such methods and compositions should be capable of treating or preventing infections in organisms, including humans, animals and plants.

SUMMARY OF THE INVENTION

The present invention is directed towards compositions and methods of treatment and prevention of microbial infections. Methods include administration of compositions comprising at least one protein isolated from a bacterial lysates. The present invention contemplates use of bacterial lysates made from bacteria that has stable reproduction, and does not produce a toxin or have deleterious effects either on the bacteriophage or on the human or animal receiving the resulting lysate. Bacterial lysates, made by lytic infection with a bacterial phage, include, but are not limited to, those made with strains of *Staphylococcus aureus* (*S. aureus*), *Klebsiella pneumoniae*, (*K. pneumoniae*) and *Pseudomonas aeruginosa* (*P. aeruginosa*). Bacterial strains include those that have been deposited at the Czech Collection of Microorganisms (CCM) having accession numbers, CCM 4992, CCM 4993, CCM 4994, CCM 4995, CCM 4996, CCM 4997, CCM 4998. Bacteriophages used for the lytic infection to make the bacterial lysate, from which one or more proteins are isolated, comprise bacteriophages deposited at the Deutsche Sammlung von Mikroorganismen und Zellkulturen GmbH (DSM) and having accession numbers, 14614, 14615, and 14616.

The present invention comprises a composition, comprising at least one or more than one proteins isolated from a bacterial lysate derived from the infection of at least one bacterial strain of *S. aureus, K. pneumoniae*, or *P. aeruginosa* with a bacteriophage. Compositions may comprise a mixture of a bacterial lysate and one or more proteins isolated from the same bacterial lysate or a different bacterial lysate. Compositions of the present invention may comprise at least one protein isolated from a bacterial lysate derived from one or more *S. aureus* bacterial strains deposited with the CCM under accession numbers CCM 4992, CCM 4993, CCM 4994, CCM 4995, CCM 4996, CCM 4997, and CCM 4998.

The present invention also comprises at least one protein isolated from a bacterial lysate derived from bacteriophages deposited with the DSM having accession numbers DSM 14614, DSM 14615, and DSM 14616. The present invention comprises at least one protein isolated from a bacterial lysate made with *S. aureus* bacterial isolates deposited with the CCM under accession numbers CCM 4992, CCM 4993, CCM 4994, CCM 4995, CCM 4996, CCM 4997, and CCM 4998, that have undergone lytic infection a bacteriophage, deposited with the DSM under accession number DSM 14614, DSM 14615, and DSM 14616.

The at least one protein isolated from a bacterial lysate of the present invention may be used in methods of treating or preventing pathological conditions of microbial infections in humans or animals. For example, at least one protein isolated from a bacterial lysate may be provided to humans or animals to prevent, treat or lessen the infection by bacteria. The compositions of the present invention may further comprise a suitable pharmaceutical carrier. The compositions may be provided by known routes of administration, such as orally, nasally, topically to any body surface, or by injection. The pathological conditions of microbial infections which can be treated or prevented or lessened by the present invention include, but are not limited to, conditions such as chronic or recurrent upper respiratory disease, chronic or recurrent ear infections wound infection, post-operational infections, bacterial pneumonia infections, allergies, sepsis, skin infections, osteomyelitis, endocarditis, skin polymicrobial infections, bronchial asthma, chronic sinusitis, cystic fibrosis or acne vulgaris. The compositions of the present invention may be used as vaccine compositions in the treatment or prevention of microbial infections. The compositions can be used in methods for the treatment and prevention of local or systemic bacterial infections. Additionally, the compositions of the present invention may be used in methods for immune stimulation.

DESCRIPTION OF DRAWINGS

FIG. 4 is a graphic representation of the isolated proteins of particular fractions from a staphylococcal lysate identified by amino acid sequence.

DETAILED DESCRIPTION OF THE INVENTION

Figure 1:
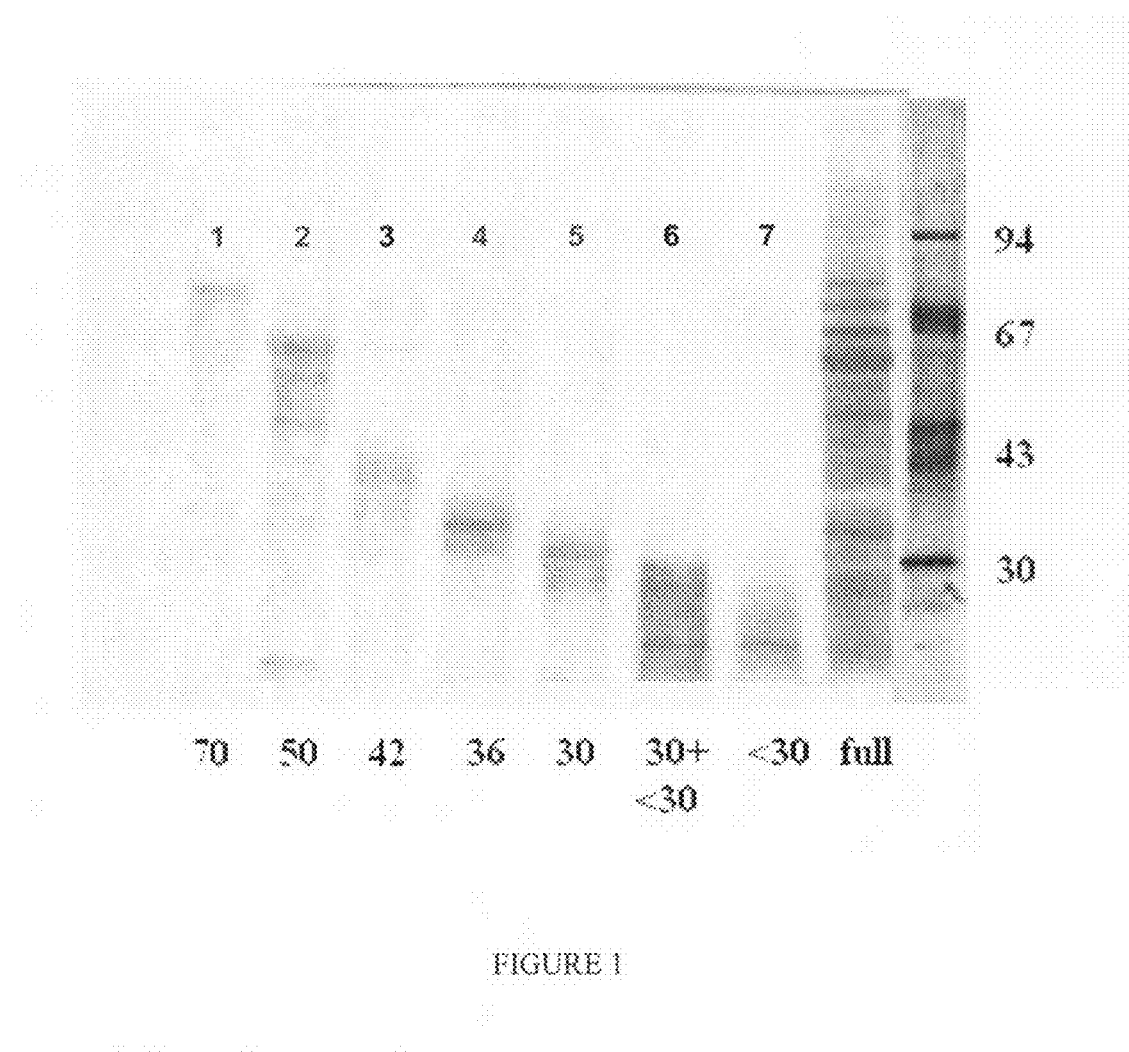
FIG. 1 is a Western blot of staphylococcal lysate antigenic proteins.

The present invention comprises compositions and methods for the treatment of microbial infections comprising administering an effective amount of at least one protein isolated from one or more bacterial lysates or mixtures thereof. As used herein, the term "isolated" includes physical isolation of a protein from a bacterial lysate or includes that the at least one protein is a protein that has been identified as being a component of a bacterial lysate. Once identified, the protein may be provided by techniques known to those in the art, such as by recombinant methods. The compositions of the present invention are immunogenic and may comprise at least one or more immunogenic or immunostimulating proteins, materials or formulations for regulating or affecting microbial distribution in an organism.

The present invention comprises compositions and methods of vaccination against microbial infections comprising administering compositions comprising at least one protein identified as being a component of one or more bacterial lysates or mixtures thereof and a pharmaceutically acceptable carrier. The lysates may be used individually or in combination, or one or more lysates may be combined with one or more proteins isolated from a lysate. The vaccines of the present invention are used to immunize animals and humans against bacterial diseases by administering to the human or animal an effective immunizing amount of at least one protein isolated from at least one bacterial lysate, or a combination of at least one protein and at least one bacterial lysate.

The compositions of the present invention comprise at least one protein isolated from at least one bacterial lysate produced by infecting selected bacteria with selected bacteriophages. The present invention contemplates use of a bacteriophage that stably reproduces in a selected bacterial strain and does not result in the production of a significant amount of a toxin or another component that has deleterious effects either on the host bacteria or in the resulting lysate that is deleterious to the human or animal receiving the lysate. Determination and selection of such bacteriophages are performed using techniques known to microbiologists and include testing for long term stability in a general host strain, long term persistence of virulence, stability and reproducibility of lysis and reproducibility of resultant lysates. The host strain is a strain which is extremely sensitive to the lytic properties of the bacteriophage. It is selected from the strains sensitive to the particular bacteriophage.

The compositions of the present invention further comprise one or more proteins isolated from one or more bacterial lysates derived from selected bacteria. The present invention contemplates use of any bacterium that has stable reproduction and does not produce a toxin that has deleterious effects either on the bacteriophage or in the lysate recipient. Determination and selection of such bacteria is performed using techniques known to those skilled in the art and includes testing for the absence of toxins particularly: alpha toxin, beta toxin, delta toxin, gamma toxin, enterotoxins A, B, C, and D, Toxic Shock Syndrome Toxin (TSST), exfoliatins A and B, leukocidin, fatty acid modifying enzyme, and hemolysins. Testing also includes tests for stability and reproducibility of lysates generated by the phage-induced lysis, long-term sensitivity of the bacterial strains, and continued susceptibility of the bacteria to lysis by phages without the appearance of phage-resistant colonies.

Selection of a lysate composition is determined by the methods of use for a particular lysate composition. For example, if the desired use is to provide immunity for staphylococcal infections, one or more strains of staphylococcal bacteria are used as the bacterial host organisms. In this same example, one or more bacteriophages that are specific for staphylococcal bacteria, or are at least capable of having a productive infection in staphylococcal bacteria, are used to create the staphylococcal lysate. Alternatively, one bacterial strain may be grown to produce a bacterial culture or bacterial broth and then separate aliquots of the bacterial culture are each infected with a different bacteriophage to create individual lysates. These individual lysates may be used individually or combined to form compositions. In another embodiment, different bacterial strains are grown and then each is infected with the same bacteriophage to yield lysate compositions that can be used individually or combined to form compositions. Another embodiment of the present invention contemplates the use of different bacterial strains that are each infected with different bacteriophages and the resulting lysates are used individually or in combination to form compositions.

The compositions of the present invention preferably comprise at least one protein isolated from a lysate from at least one bacterial strain, or two or more bacterial strains. A composition comprises at least one protein isolated from at least one lysate from one of the following bacteria: *Staphylococcus aureus* (*S. aureus*), *Klebsiella pneumoniae* (*K. pneumoniae*), and *Pseudomonas aeruginosa* (*P. aeruginosa*). Compositions comprise at least one protein isolated from at least one lysate derived from bacterial strains of *S. aureus* deposited with the Czech Collection of Microorganisms (CCM) on Oct. 11, 2001 and having accession numbers. CCM 4992, CCM 4993, CCM 4994, CCM 4995, CCM 4996, CCM 4997 and CCM 4998. Compositions may comprise at least one protein isolated from at least one of the bacterial strains deposited with the CCM on Oct. 11, 2001 and having accession numbers CCM 4992, CCM 4993, CCM 4994, CCM 4995, CCM 4996, CCM 4997 and CCM 4998, in combination with lysates made by lytic infection of at least one of the bacterial strains deposited with the CCM on Oct. 11, 2001 and having accession numbers CCM 4992, CCM 4993, CCM 4994, CCM 4995, CCM 4996, CCM 4997 and CCM 4998.

The methods of the present invention comprise the use of bacteriophages in a lytic infection of bacteria to yield the desired bacteriophage lysates. A method comprises lysates produced by bacteriophages for *S. aureus*, *K. pneumoniae*, and *P. aeruginosa*. Methods comprise lysates derived from lytic infection of bacteria by bacteriophages deposited on Nov. 19, 2001 with the Deutsche Sammlung von Mikroorganismen und Zellkulturen GmbH (DSM) and having accession numbers 14614, 14615, and 14616. Compositions comprise at least one protein isolated from a lytic infection of bacteria by the bacteriophages deposited on Nov. 19, 2001 with the Deutsche Sammlung von Mikroorganismen und Zellkulturen GmbH (DSM) and having accession numbers 14614, 14615, and 14616. The bacteriophages can be used alone or in combination to lyse one or more bacterial strains.

Generally, methods of the present invention comprise growing one or more desired bacterial strains to a desired concentration. For example, ranges of concentrations of bacterial cultures are from $1\times10^6$ to $1\times10^{12}$ cells/ml, $1\times10^7$ cells/ml, $1\times10^8$ cells/ml, $1\times10^9$ cells/ml, $1\times10^{10}$ cells/ml, or $1\times10^{11}$ cells/ml. At the selected time, one or more bacteriophages, at an effective concentration, are added to the bacterial culture. For example, ranges of concentrations of bacterial phage cultures are from $1\times10^8$ to $1\times10^{12}$, $1\times10^9$, $1\times10^{10}$, or $1\times10^{11}$. Infection and lysis by the bacteriophages is allowed to proceed, yielding a lytic infection. Incubation of the bacteriophage or phages with the bacterial culture can be from 3 to 48 hours. The resulting bacterial lysate is then filter sterilized using filters having a pore size from <0.1 μm to 0.45 μm (micrometer).

Both the material retained on the filter, the rententate, and the flow through material, the filtrate, are kept. It is preferred to use the filtrate for bacterial lysates in methods of treatment and immune stimulation. In general, the filtrate comprises cellular materials such as components of cell walls, cellular membranes, proteins, ribosomal fractions, glycoproteins, DNA, RNA, and the like. The rententate from ultrafiltration using filters with a pore size of <0.1 micrometers comprises larger cellular materials and unlysed cells and bacteriophages which may also be used in the compositions and methods of the present invention.

The use of bacteriophages to prepare lysates is effective for all types of bacteria and allows the preparation of lysates to evolve with the bacteria and avoid resistance problems common to pharmaceuticals, such as development of antibiotic resistance by bacteria. The use of bacteriophage lysates allows the preparation of products capable of modulating the immune system prepared from a single bacterial strain, or a combination of bacterial strains.

In general, methods of preparing a bacterial lysate of the present invention comprise screening strains of a particular bacterial family or group that does not produce toxins, for selected bacteria that exhibit the most common antigenic pattern found in the bacterial family or group. The antigenic pattern can be determined by immunogenic methods such as fluorescent antibody identification, FACS selection, ELISA, Western blots, SDS gel electrophoresis or by other detection methods known to those skilled in the art. Cultures of the selected bacteria are then infected by the introduction of phage homologues. The combination is screened for strains that result in quantitative lysis of bacteria in a given time and strains that exhibit the most common antigenic pattern. The bacterial strain and phage are then preserved, preferably by lyophylization, to maintain stability. The stability of the bacterial strains and phages are determined through stability assays, repeated cultures and subcultures on media. The bacterial strains and phages are also checked for antigenic composition and reproducibility of antigenic patterns of lysates. At least one, two or more, of the resultant lysates may be combined with one or more proteins isolated from a bacterial lysate to yield an immunomodulator composition.

The proteins isolated from a bacterial lysate comprise proteins that are antigenic, i.e., produce an antibody response in an animal, or that stimulate the immune system, such as enhancing the immune response or create a change in an immune cell. Isolated proteins include those that can function as a vaccine. For example, an antigenic protein is identified, isolated, and when used as an antigen in vaccination methods in an animal or human, provides immunity for the animal or human from infection by the bacterial organism. For example, the antigenic protein may provide an immune response in the animal or human that aids in the prevention or treatment of a pathological condition caused by infection or growth of bacteria. The antigenic protein may be determined to be antigenic by immunological methods such as fluorescent antibody identification, FACS selection, ELISA, Western blots, SDS gel electrophoresis or by other detection methods known to those skilled in the art.

For example, a bacterial lysate is prepared and the proteins from the lysate are separated by gel electrophoresis, and transferred onto a support membrane. Immune sera, from a mammal in which the bacterial lysate was injected, is used in Western blot techniques to detect and identify the proteins that are antigenic in the bacterial lysate. The antigenic proteins are then identified using techniques such as MALDI-TOF, LC-MS/MS, or other protein isolation and identification methods known to those skilled in the art. Databases such as MASCOT, can be used to identify the proteins by the amino acid sequences derived from such methods. The identified proteins may be further purified, such as by protein affinity columns, or by recombinant methods wherein the protein's corresponding DNA sequence is expressed by an expression vector in an organism so that large quantities of the proteins can provided.

An aspect of the present invention comprises compositions comprising at least one antigenic protein isolated from the lytic infection by a bacteriophage deposited as described herein of at least one staphylococcal strain deposited as described herein. For example, antigenic proteins from a lytic infection of bacterial strains CCM 4992 and 4993 by phage 14614 were isolated by methods described herein. Antigenic proteins were determined by Western blot techniques, and such proteins were identified as having molecular weights of 70 kDa, 50 kDa, 42 kDa, 36 kDa, 30 kDa, and <30 kDa. When tested in an immunogenic challenge assay, such as when used in vaccination of animals, the 70 kDa, 50 kDa, 36 kDa, and 30 kDa proteins provided immune protection against infection by *S. aureus*. The test involved vaccinating the animals with each protein and then challenging the vaccinated animals with *S. aureus* by scratching the skin and adding *S. aureus* to the interrupted skin. In the animals vaccinated with a protein that provides protection, the size of the infected area was nonexistent or reduced compared to control animals. These methods can be used to identify other antigenic proteins that are immunoprotective in bacterial lysates.

The compositions comprising at least one protein isolated from a bacterial lysate can be used in methods for the treatment of local or systemic bacterial infections including, but not limited to, chronic or recurrent respiratory or ear infections, prophylactic prevention of infections, and treatment of pathological conditions of microbial infections such as postoperational infections, bacterial pneumonia infections, sepsis, skin infections, wound infection, osteomyelitis, skin polymicrobial infections, allergies, asthma, endocarditis, arthritis, abscess, sinusitis, and acne vulgaris. Additionally, compositions comprising at least one protein isolated from bacteriophage lysates can be used in methods for immune stimulation such as vaccines that boost the immune system. The compositions can also be administered for several months prior to planned operations, such as knee or hip replacements, to boost general immune response, decrease recovery time, and prevent nosocomial infections.

Methods of treatment contemplated by the present invention comprise administration of an effective amount of a composition comprising at least one protein isolated from a bacterial lysate to an organism having an infection or in need of immune stimulation. An effective amount of a composition comprising at least one protein isolated from a bacterial lysate can be determined by using known amounts of such compositions, or by starting treatment with a small dose and increasing the dose until the desired effect is achieved. An effective amount may comprise an amount of the composition that provides an immune response, such as development of an antibody response or a long-term immune memory response in a human or animal. Such techniques for determining effective amounts are known to those skilled in the art and do not require undue experimentation to determine. Differing routes of administration of the compositions include, but are not limited to, oral, buccal, nasal, aerosol, topical, transdermal, injectable, slow release, controlled release, iontophoresis, sonophoresis, intravenous, intramuscular, intraperitoneal, intraspinal, intrathecal, intracerebroventricular, intraarterial, subcutaneous and intranasal routes, and such different routes may require differing effective amounts to achieve the desired result. For example, oral administration may require different effective amounts than topically administered effective amounts. In general, a range of 0.0001 mg/kg/day to 500 mg/kg/day may provide an effective amount of a bacterial lysate composition. A range of 0.0001 µg/kg/day to 500 µg/kg/day may provide an effective amount of an isolated protein composition. For example, 0.1 ml to 0.3 ml of a 25 µg/ml solution of an isolated protein may be provided in a subcutaneous administration route for vaccination or treatment.

Methods of the present invention comprise administration of a composition comprising at least one protein isolated from a bacterial lysate three to six weeks prior to reconstructive surgery such as, but not limited to, a knee or hip replacement. For example, an effective amount of the composition is administered in a pharmaceutical formulation and may be injected intradermally or subcutaneously twice a week. Three days after administration of the initial dose, the patient is observed for tolerance of the composition. If no local reaction is noted, the dose can be increased and may be administered every other day. For nasal routes of administration, preferably two to four drops of a pharmaceutical formation of the composition are placed in each nostril the first four days, and after four days, the dosage is repeated every other day. The length of treatment may be three to four months. Multiple methods of administration may be combined with the length of treatment depending on the immune status of the patient.

The present invention further comprises methods of eliciting an immune response in a host comprising administering an effective amount of an immunogenic composition comprising at least one protein isolated from a bacterial lysate, or a combination of at least one protein isolated from a bacterial lysate and at least one bacterial lysate. The immunogenic composition may be used prophylactically as part of a vaccination method in which the composition is administered prior to infection, or in the treatment of an acute infection. The immune response may be a humoral or a cell-mediated immune response. Immunogenicity may be improved by the co-administration of the immunogenic composition with one or more adjuvants. Adjuvants may act by retaining the antigen locally near the site of administration facilitating a slow sustained release of antigen to cells. Adjuvants can also attract immune cells to the site of injection and stimulate such cells to elicit immune responses. A wide range of adjuvants can aid in evoking an immune responses. These include, but are not limited to, pluronic polymers with mineral oil, Freund's complete adjuvant, lipid A, liposomes and cholera toxin subunit B or its genetically modified variants.

The following specific examples of the methods and compositions of the present invention are in no way to be seen as limiting, but merely provide illustrative embodiments for the applications of the present invention. The present invention contemplates the use of at least one protein isolated from at least one bacterial lysate for the treatment of bacterial and other microbial infections and for stimulation of the immune system in general and other disease treatments or compositions are not limited by the specific examples taught herein.

*Staphylococcus Aureus* Infections Prevention and Treatment

Staphylococcal bacteria, and *S. aureus* in particular, are some of the more common and virulent pathogens. Some staphylococcal infections are characterized by intense suppuration, necrosis of local tissues and the formation of abscesses. Staphylococcal infections are responsible for skin infections, such as furuncles, carbuncles and impetigo, and deep lesions spreading from the skin into bones, joints, soft tissues and organs. *S. aureus* can produce toxins leading to scalded skin syndrome, toxic shock syndrome and staphylococcal food poisoning. It is a major cause of wound infection and a continuing cause of hospital epidemics. *S. aureus* is currently resistant to many classes of antibiotics and is currently being treated with vancomycin as a last resort. However, strains resistant to vancomycin have already begun to appear. Methicillin-resistant staphylococcal bacteria are problematic in hospital settings and are being found more frequently in non-hospital settings such as schools, prisons, and other crowded conditions.

*S. aureus* has many virulence factors that act against native or adaptive immune responses. While not wishing to be bound by any particular theory, it is currently believed that part of the innate response against *S. aureus* comprises the Toll-like receptor (TLR) family. TLRs are transmembrane receptors linking the pattern recognition system of pathogens with intracellular signaling. In humans, the TLR family is represented by TLR (TLR 1-10), several proteins related to TLR (RP105, Nod1, Nod2), as well as lipopolysaccharide (LPS) receptor (CD14). Several TLRs appear to have a specific function in the pattern recognition system. For example, TLR-2 is believed to activate cells in response to gram-positive cell-wall components (peptidoglycan). TLR-4 is important (in complex with CD14) for recognition of LPS (gram-negative bacteria). TLR-9 recognizes the CpG motif of bacterial DNA. The activation of the innate immune system induces early inflammatory reaction mediated by monocytes, neutrophils, and endothelial cells. The response can occur with or without participation of the adaptive immune system, leading to leukocyte recruitment, production of pro-inflammatory cytokines (TNF-alpha, IL-1 beta), reactive oxygen products, and effector cytokines (e.g., IL-12) acting on T cells, antigen presenting cells, and on B cells, by a cascade of cytokines.

Mice deficient in TLR-2 or a signaling molecule (MyD88) were highly susceptible to *S. aureus* infection (J. Immunol. 165, 5392-5396, 2000). Furthermore, wild-type mice became more resistant to acute polymicrobial sepsis after treatment with CpG DNA (J. Immunol. 165, 4537-4543, 2000) that is currently believed to act via TLR-9. TLR-2 is likely to play an important role in human *S. aureus* infection as evidenced by detection of TLR-2 polymorphism associated with *S. aureus* septic shock (Infect. Immun. 68, 6398, 2000). Activation of TLR-2 receptor with *S. aureus* cell wall components results in upregulation of Th-1 pathway (TNF-alpha, interferon gamma, IL-1, etc.). Increase of these pro-inflammatory cytokines activates and modulates multiple responses of innate and adaptive immunity.

S. aureus has several mechanisms to interfere with the normal immune response. Not only has the bacteria developed a resistance against antimicrobial proteins, but it can also survive inside neutrophils. In addition, various strains of S. aureus possess some of the battery of toxins, enzymes and other products that enhance infectivity and bacterial survival and proliferation. Antibodies specific against toxins and enzymes and other soluble products neutralize the activities of the toxins while antibodies specific against cells and cellular components opsonize the targeted cells and enhance their phagocytosis.

Treatment of staphylococcal infections and S. aureus in particular, are provided by the present invention. Proteins isolated from staphylococcal lysates that are antigenic and immunoprotective are used to vaccinate, for prophylactic treatments, and are used in treatment of existing staphylococcal infections. For example, one or more proteins isolated from a staphylococcal lysate made by the lytic infection of staphylococcal bacteria deposited as CCM 4992, CCM 4993, CCM 4994, CCM 4995, CCM 4996, CCM 4997, and CCM 4998, by bacteriophage deposited as DSM 14614, DSM 14615, and DSM 14616, are used in vaccination methods or for active or chronic infections by staphylococcal bacteria. Such proteins include those isolated by SDS page electrophoresis that are antigenic, as shown by immunosera to whole lysate, and include proteins with molecular weights of 70 kDa, 50 kDa, 42 kDa, 36 kDa, 30 kDa, and <30 kDa. Such proteins may be immunoprotective for staphylococcal infections, or may provide immune boosting or enhancement to the immune system.

It is currently believed that of the antigenic proteins in a staphylococcal lysate formed by the lytic infection with a bacteriophage, staphylococcal proteins may provide an immune protection function, i.e. provide humoral or cellular activation of the immune system that would directly affect staphylococcal bacteria. For example, the immune protection function may take the form of antibodies that bind to, interfere with, inactivate, or opsonize the staphylococcal bacteria. Other antigenic proteins, which may be bacteriophage derived, may have other immune protective functions that direct or indirect, such as by providing a stimulus to the immune system to make the immune system respond more vigorously to an immune challenge. Examples of proteins isolated from at least one staphylococcal lysate of bacteria deposited as CCM 4992, CCM 4993, CCM 4994, CCM 4995, CCM 4996, CCM 4997, and CCM 4998, and at least one bacteriophage deposited as DSM 14614, DSM 14615, and DSM 14616, include, but are not limited to, major tail sheath protein, capsid protein, enolase, fructose-bisphosphate (f-b) aldolase, putative transport system binding (ptsb) lipoprotein, phosphoenolpyruvate-protein (ppp) phosphatase, elongation factor, putative bacteriophage (pb) baseplate protein, 30S ribosomal protein, 50S ribosomal protein, ABC transporter (periplasmic amino acid binding protein), and triosephosphate isomerase, or combinations thereof. A composition comprising one or more of these proteins, isolated from a lytic bacteriophage infection of staphylococci, can be administered to a subject in vaccination methods, or to treat active or chronic infections. Vaccination methods include administering at least one of the isolated proteins in a composition to a subject not currently infected, and may include booster shots at a later time to enhance the immune response. When infected later, the subject shows a lesser response to the infection than does a subject not previously vaccinated. Administration of an isolated protein composition for active or chronic infections includes providing the isolated protein composition, such as by providing the composition by intramuscular or subcutaneous routes, the active or chronic infection is resolved. It is believed that administering the isolated protein composition may cause the immune system to respond to the infection more effectively.

One or more isolated proteins, identified herein, may be combined with selected staphylococcal lysate compositions comprising lysate from single or multiple strains of staphylococcus and bacteriophages, and such compositions may be administered through various routes, including but not limited to, nasal drops and subcutaneous routes, or a combination thereof. Lysates from different strains of staphylococcus or lysates that result from different bacterial phage inoculations are preferably combined in equal proportions.

Staphylococcal lysate (SPL) has been clinically effective in the treatment of staphylococcal infections of adults, as well as chronic conditions in pediatrics (chronic upper respiratory diseases, bronchial asthma, chronic sinusitis, cystic fibrosis) and in dermatology (acne vulgaris). SPL is prepared by lysis of at least one S. aureus culture with at least one polyvalent bacteriophage. Most staphylococcal phages belong to the Siphoviridae family, e.g., phages with double-stranded linear DNA and with long, noncontractile tails. SPL is a complex of antigenic components of ribosomal, cytoplasmic, nuclear, cell wall, and membranous origin. Purified components of SPL can be used for specific stimulation of certain pathways including, but not limited to, peptidoglycans and lipoteichoic acids via TLR-2, and CpG DNA via TLR-9.

Alternatively, animals and humans can be vaccinated with an isolated protein identified herein combined with SPL compositions made by a lytic infection of the bacteria deposited as described herein by the bacteriophage deposited as described herein so that staphylococcal infections are resisted. Such treatment comprises administration of a composition comprising at least one protein isolated from a lytic infection of the bacteria by bacteriophage, both deposited as disclosed herein, or optionally combined with an SPL composition comprising lysed bacteria and phage, as deposited and disclosed herein, through routes of administration comprising subcutaneous injections, nasal drop application and lavage of osteomyelitis fistulas. The administration of the compositions can take place prophylacticaly, prior to the occurrence of a staphylococcal infection, as well as during a staphylococcal infection. Preferred times of prophylactic administration are after the age of three for three to six weeks prior to potential infections situations or generally as part of a vaccination program.

*Klebsiella Pneumoniae* Infection Prevention and Treatment

Another bacteria group for which the present invention is effective is the *Klebsiella* bacteria, in particular, *K. pneumoniae*. *K. pneumoniae* is a nonopportunistic pathogen normally found in the gut. Outside of the gut, it is a growing source of hospital-acquired infections causing pneumonia and urinary tract infections. Patients with chronic respiratory diseases, diabetics, alcoholics, and people of advanced age, as well as those using respiratory therapy devices, intravenous and urinary catheters are particularly sensitive to acquiring infectious *Klebsiella*.

Classically, *K. pneumoniae* infection of the respiratory tract causes a severe, rapid-onset illness that often results in destruction of areas in the lung. Even with treatment, the mortality rate due to *K. pneumoniae* is 50%. Infected persons generally develop high fever, chills, flu-like symptoms and a cough that produces a lot of mucous. While normal bacterial pneumonia frequently resolves without complication, *K. pneumoniae* frequently causes lung destruction and abscesses.

*Klebsiella* can also cause less serious respiratory infections, such as bronchitis, which is usually a hospital-acquired infection. Other common hospital-acquired infections caused by *Klebsiella* are urinary tract infections, surgical wound infections and bacteremia. These infections can progress to shock and death if not treated early in an aggressive fashion.

Methods of treatment of *Klebsiella* infections and *K. pneumoniae* in particular, are provided by the present invention. Selected *klebsiella* lysate compositions comprising single or multiple strains of *klebsiella* or bacteriophages are administered through various routes, including but not limited to, nasal drops and subcutaneous routes, or a combination thereof. The lysate compositions are administered daily until the desired treatment is achieved.

Alternatively, animals and humans can be vaccinated or treated prophylactically with bacterial lysate compositions so that *klebsiella* infections are resisted. Such treatment comprises administration of *klebsiella* lysate compositions comprising lysates from single or multiple strains of *klebsiella* and phage through routes of administration comprising nasal drops and subcutaneous administration at times prior to infection with *klebsiella*. Preferred prophylactic administration for humans is after the age of 3, for 3-6 weeks prior to potential infectious conditions such as hospitalizations or generally as part of a vaccination program.

*Pseudomonus aeruginosa* Infection Prevention and Treatment

Another frequent hospital contaminant, *P. aeruginosa* is a versatile, gram-negative bacterium that grows in soil, marshes, and coastal marine habitats, as well as on plant and animal tissues. *P. aeruginosa* is able to grow in aqueous solutions including distilled water. This ability results in frequent contamination of intravenous (i.v.) fluids, respirators, anesthesia equipment and other hospital equipment. People with cystic fibrosis, burn victims, individuals with cancer, and patients requiring extensive stays in intensive care units are particularly at risk of *P. aeruginosa* infection. Unlike many environmental bacteria, *P. aeruginosa* has a remarkable capacity to cause disease in susceptible hosts. It has the ability to adapt to and thrive in many ecological niches, from water and soil to plant and animal tissues. *P. aeruginosa* can produce a number of toxic proteins which not only cause extensive tissue damage, but also interfere with the immune system's defense mechanisms. These proteins range from potent toxins that enter and kill host cells at or near the site of colonization to degradative enzymes that permanently disrupt the cell membranes and connective tissues in various organs.

*P. aeruginosa* infections are a particular problem in individuals with cystic fibrosis. Cystic fibrosis is a common lethal genetic disease (incidence 1:2,000 Caucasian births). The disease presents with a history of chronic lung disease, recurrent pneumonia, cough, and bronchiectasis. The lungs of cystic fibrosis patients may be colonized with *P. aeruginosa*, particularly a special mucoid strain that contributes to fatal complications. *S. aureus* is frequently present as well.

Treatment of pseudomonas infections and *P. aeroginosa* in particular, are provided by the present invention. Selected pseudomonas lysate compositions comprising lysates from single or multiple strains are administered through various routes, including but not limited to, nasal drops and subcutaneous routes, or a combination thereof.

Alternatively, animals and humans can be vaccinated with pseudomonas lysate compositions so that pseudomonas and pneumococcal infections are resisted. Such treatment comprises administration of pseudomonas lysate composition comprising lysates from bacteria and phage through routes of administration comprising nasal and subcutaneous injection at times prior to infection with pseudomonas. Preferred times of preventative administration are after 3 years of age, for three to six weeks prior to the potential infectious situations such as proposed hospitalization or generally as part of a vaccination program.

Mastitis

The present invention is effective for the prevention and treatment of mastitis, particularly mastitis in dairy cattle, though any mastitis can be treated using the present invention. Mastitis in dairy cattle is an inflammation of the mammary gland in response to intramammary bacterial infection, mechanical trauma, or chemical trauma. Economic losses due to mastitis are $1.7 billion dollars a year in the U.S. alone. It is thought that contagious mastitis is primarily caused by *S. aureus* and *Streptococcus agalactiae*. Environmental mastitis can be caused by a variety of different bacteria, including, but not limited to, *K. pneumoniae, Escherichia coli, Klebsiella oxytoca, Enterobacter aerogenes, Streptococcus uberis, Streptococcus bovis*, and *Streptococcus dysgalactia*.

Traditional prevention of bovine mastitis involves a complex regimen of daily teat-dipping with a disinfectant solution, and may involve antibiotic-containing teat dips. When infection does occur, intramammary infusion of antibiotics is indicated, however this leads to increasingly resistant strains of bacteria. Antibiotic therapy can reduce the infection so that the milk produced is saleable, but it generally does not lead to complete elimination of the causative organism. While not wishing to be bound to any particular theory, studies on mastitis have indicated that part of the problem in treating mastitis is that a significant number of bacteria remain viable in the mammary gland within phagocytic polymorphonuclear neutrophil leukocytes (PMN). When lysis of the leukocyte occurs, the phagocytized bacteria may provide a renewed source of mastitis producing, for example, staphylococcal regrowth. While not wishing to be bound, it is currently believed that the use of compositions comprising at least one isolated protein, or optionally comprising staphylococcal lysates allows for the creation of memory cells, allowing the cow to respond to remaining bacteria, whenever they might appear.

In general, bovine mastitis is treated by administering an effective amount of a composition comprising an isolated protein from a lytic infection of a staphylococcal bacteria as deposited and described herein by a bacteriophage deposited and described herein, and optionally comprising a bacterial lysate from one or more of deposited bacteria and bacteriophage described herein, to a cow. The administration may be a prophylactic administration, in that all cattle in the herd are treated with a composition, or the administration may occur when infection occurs in individual cows. For example, in heifers, vaccination may start at 6 months of age. Three subcutaneous injections of the composition, comprising at least one protein, or combined composition of at least one protein and a lysate (5 cc each) are provided, by topical, nasal, subcutaneous or intramuscular routes of administration between 6 and 24 months of age.

The present invention is also useful in the treatment of skin infections in other domesticated animals including canine and feline staphylococcal skin infection, dermatitis, and other chronic infections. Treatment methods comprise the administration of an effective amount of a composition of the present invention to domesticated animals through routes known to provide an effective amount of the immunoprotective or immunostimulatory composition. Such routes may be nasal, oral, topical or injected via subcutaneous or intramuscular administration.

Bacterial antigens and others are known to trigger immunomodulatory effects in vivo. For example, in an infection of a host by a staphylococcal organism, other bacteria and some viruses, it is believed that a staphylococcus lysate composition potentiates cell-mediated as well as humoral immunity in animals and humans. Treatment with staphylococcus lysates elevates antigen specific as well as total humoral antibody and immunoglobulin levels creating an effective immunoadjuvant for humoral responses as well.

Delivery and Dosage

The methods of the present invention comprise routes of administration that include, but are not limited to, oral, buccal, nasal, aerosol, topical, transdermal, injectable, slow release, controlled release, iontophoresis, sonophoresis, and other delivery devices and methods. Injectable methods include, but are not limited to, intravenous, intramuscular, intraperitoneal, intraspinal, intrathecal, intracerebroventricular, intraarterial, subcutaneous and intranasal routes. Methods for the delivery of proteins to subjects are known in the art.

The compositions for treating the pathologies by the present invention can further include a pharmaceutically acceptable carrier or excipient. The compositions can also include other medicinal agents, pharmaceutical agents, carriers, adjuvants diluents and other pharmaceutical preparations known to those skilled in the art. These agents are known to those skilled in the art and are generally described as being biologically inactive and can be administered to patients without causing deleterious interactions with the active agent.

According to the invention, at least one pharmaceutical composition can be delivered by any of a variety of inhalation or nasal devices known in the art for administration of a therapeutic agent by inhalation. Devices capable of depositing aerosolized formulations in the sinus cavity or alveoli of a patient include metered dose inhalers, nebulizers, dry powder generators, sprayers, and the like. Other devices suitable for directing pulmonary or nasal administration are also known in the art.

There are a several desirable features of an inhalation device for administering a compound of the present invention. For example, delivery by an inhalation device is advantageously reliable, reproducible, and accurate. For pulmonary administration, at least one pharmaceutical composition is delivered in a particle size effective for reaching the lower airways of the lung or sinuses.

All such inhalation devices may be used for the administration of a pharmaceutical composition in an aerosol. Such aerosols may comprise either solutions (both aqueous and non aqueous) or solid particles. Metered dose inhalers like the Ventolin® metered dose inhaler, typically use a propellant gas and require actuation during inspiration. See, e.g., WO 98/35888; WO 94/16970. Dry powder inhalers like Turbuhaler® (Astra), Rotahaler® (Glaxo), Diskus® (Glaxo), Spiros® inhaler (Dura), devices marketed by Inhale Therapeutics, and the Spinhaler® powder inhaler (Fisons), use breath-actuation of a mixed powder. See U.S. Pat. Nos. 5,458,135; 4,668,218; WO 97/25086; WO 94/08552; WO 94/06498; and EP 0 237 507, each entirely expressly incorporated herein by reference. Nebulizers like AERx®, Aradigm, the Ultravent® nebulizer (Mallinckrodt), and the Acorn II® nebulizer (Marquest Medical Products), the above references entirely expressly incorporated herein by reference, produce aerosols from solutions, while metered dose inhalers, dry powder inhalers, etc. generate small particle aerosols. These specific examples of commercially available inhalation devices are intended to be a representative of specific devices suitable for the practice of the invention, and are not intended as limiting the scope of the invention.

Suitable formulations, wherein the carrier is a liquid, for administration, as for example, a nasal spray or as nasal drops, include aqueous or oily solutions of the active ingredient.

A spray comprising a pharmaceutical composition of the present invention can be produced by forcing a suspension or solution of a compound disclosed herein through a nozzle under pressure. The nozzle size and configuration, the applied pressure, and the liquid feed rate can be chosen to achieve the desired output and particle size. An electrospray can be produced, for example, by an electric field in connection with a capillary or nozzle feed.

A pharmaceutical composition of the present invention can be administered by a nebulizer such as a jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of a composition protein through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation of composition protein either directly or through a coupling fluid, creating an aerosol including the composition protein.

In a metered dose inhaler (MDI), a propellant, and any excipients or other additives are contained in a canister as a mixture including a liquefied, compressed gas. Actuation of the metering valve releases the mixture as an aerosol.

Pharmaceutical compositions for use with a metered-dose inhaler device will generally include a finely divided powder containing a compound disclosed herein as a suspension in a non-aqueous medium, for example, suspended in a propellant with the aid of a surfactant. The propellant can be any conventional material employed for this purpose such as chlorofluorocarbon, a hydrochlorofluorocarbon, a hydrofluorocarbon, or a hydrocarbon including trichlorofluoromethane, dichlorodifluoromethane, dichlorotetrafluoroethanol and 1,1,1,2-tetrafluoroethane, HFA-134a (hydrofluroalkane-134a), HFA-227 (hydrofluroalkane-227), or the like. One of ordinary skill in the art will recognize that the methods of the present invention can be achieved by pulmonary administration of a compound disclosed herein via devices not described herein.

An oral delivery system of compositions of the present invention may comprise capsules containing differently coated pellets of the composition, and may provide for protection of the protein components of the composition from enzymes in the gastrointestinal tract. On release from the capsule, the uncoated pellets provide an initial amount of the composition to the body, and the coated pellets provide the rest of the composition over a period of time. Another system includes hydrogel materials with coated materials, such as the compositions of the present invention, embedded in the hydrogel, such as that taught in U.S. Pat. No. 4,659,558. The unswollen hydrogel, such as that taught in U.S. Pat. No. 4,659,558, is swallowed and in the presence of fluids in the stomach, swells so that the hydrogel is retained within the stomach. The coated materials are released as the hydrogel degrades. The composition may also be administered through the use of auto-injection devices such as those described in U.S. Pat. Nos. 5,514,097; 5,159,192; and 5,643,214; as well as European Patent No. 0 516 473 B1.

In controlled release systems contemplated in the present invention, after oral ingestion, compositions may be released by diffusion and erosion throughout the gastrointestinal tract to a significant degree. Methods of the present invention for the prolongation of gastric retention time include incorporation of fatty acids to reduce physiological gastric emptying and the use of bioadhesive polymers. Such systems are known to those skilled in the art and comprise using polymers such as polycarbophyll, sodium carboxymethylcellulose, tragacanth gum, acrylates and methacrylates, modified celluloses and polysaccharide gums.

Another delivery system that is contemplated by the present invention for targeting compositions to the stomach while avoiding gastric emptying is known as a hydrodynamically balanced system. This system is based on capsules or tablets with bulk density lower than gastric fluid. Thus, the dosage form stays buoyant in the stomach. These dosage forms are comprised of 20-75% of one or more hydrocolloids, e.g., hydroxyethylcellulose and hydroxypropylmethylcellulose.

Other types of these devices include osmotic pressure compartments containing osmotically active salts. In the present invention, dissolution of these salts by the gastric fluid pumps out the lysate composition. Others are based upon a floating bilayer compressed matrix. One of the layers is comprised of a hydrophilic polymer and a carbon dioxide generating composition. The carbon dioxide maintains buoyancy, and the other hydrophilic layer releases the drug from the matrix. A further method for gastric lysate targeting involves an intragastric retention shape made of polyethylene or polyethylene blend.

The delivery systems described above may also be used in the present invention to target compositions to the upper small intestine. However, targeting to other areas of the small intestine may involve several additional systems. The low stomach pH and presence of gastric enzymes have led to the development of enteric coating. This coating protects the gastric mucosa from lysate irritation. Coating is done with a selectively insoluble substance, and protects lysates from inactivation by gastric enzymes and/or low pH.

In summary, the present invention comprises methods of administration of the compositions of the present invention for treatment of microbial infections. Not all administration routes are efficacious for every patient. Therefore, the present invention comprises various methods, which require differing formulations of the lysate compositions. The formulations include those suitable for oral, rectal, ophthalmic (including intravitreal or intracameral), nasal, topical (including buccal and sublingual), vaginal or parenteral (including subcutaneous, transdermal, intramuscular, intravenous, intradermal, intratracheal, and epidural) administration. The formulations may conveniently be presented in unit dosage form and may be prepared by conventional pharmaceutical techniques.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface active or dispersing agent. Molding, in a suitable machine, a mixture of the powdered compound moistened with an inert liquid diluent may make molded tablets. The tablets may be optionally coated or scored and may be formulated so as to provide a slow or controlled release of the lysate therein.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the lysate in a suitable liquid carrier.

The present invention additionally comprises methods of topical administration. To prepare the topical composition according to the present invention the usual manner for preparing skin care products may be employed. The active components are generally incorporated in a dermatological acceptable carrier in conventional manner. It may be packaged in discrete units including aerosol sprays, each containing a predetermined amount of the active ingredient, as a powder, stick, or granules, as creams, pastes, gels, lotions, syrups, or ointments, on sponges or cotton applicators, or as a solution or a suspension in an aqueous liquid, a non-aqueous liquid, an oil-in-water emulsion, or a water-in-oil liquid emulsion. The compositions can suitably first be dissolved or dispersed in a portion of the water or another solvent or liquid to be incorporated in the composition. The composition can also be in the form of a so-called "wash-off" product e.g. a bath or shower gel, possibly containing a delivery system for the lysates to promote adherence to the skin during rinsing. Most preferably the product is a "leave-on" product; a product to be applied to the skin without a deliberate rinsing step soon after its application to the skin. Such compositions may be prepared by any of the methods of pharmacy, but all methods include the step of bringing into association the carrier(s) with the composition. In general, the compositions are prepared by uniformly and intimately admixing the active ingredient with liquid carriers or finely divided solid carriers or both, and then, if necessary, shaping the product into the desired presentation. The composition may packaged in any suitable manner such as in a jar, a bottle, tube, roll-ball, or the like, in the conventional manner.

Formulations suitable for vaginal administration may be presented as pessaries, tamports, creams, gels, pastes, foams or spray formulations containing in addition to the lysates such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers. Extemporaneous injection solutions and suspensions may be prepared from sterile powders, granules and tablets of the kind previously described. Preferred unit dosage formulations are those containing a daily dose or unit, daily sub-dose, as herein above recited, or an appropriate fraction thereof, of the administered ingredient.

The compositions may also be entrapped in microcapsules prepared, for example, by coacervation techniques or by interfacial polymerization, for example, hydroxymethylcellulose or gelatin-microcapsules and poly(methylmethacylate) microcapsules, respectively, in colloidal drug delivery systems (for example, liposomes, albumin microspheres, microemulsions, nano-particles and nanocapsules) or in macroemulsions. REMINGTON'S PHARMACEUTICAL SCIENCES (A. Osol ed., 16th ed. (1980)).

In a specific embodiment, the compositions disclosed herein are formulated as liposomes. Liposomes containing a compound of the present invention are prepared by methods known in the art. See, e.g., U.S. Pat. Nos. 5,013,556; 4,485,045; 4,544,545; WO 97/38731; Epstein et al., 82 PROC. NATL. ACAD. SCI. USA 3688 (1985); and Hwang et al., 77 PROC. NATL. ACAD. SCI. USA 4030 (1980). The compositions of the present invention can also be administered in the form of liposome delivery systems such as small unilamellar vesicles, large unilamellar vesicles, and multilamellar vesicles. Liposomes can be formed from a variety of phospholipids such as cholesterol, stearylamine or phophatidylcholines.

The present invention provides stable formulations as well as preserved solutions and formulations containing a preservative as well as multi-use preserved formulations suitable for pharmaceutical or veterinary use, comprising at least one compound disclosed herein in a pharmaceutically acceptable formulation. Formulations in accordance with the present invention may optionally contain at least one known preservative.

In addition, co-administration or sequential administration of the compositions of the present invention and other therapeutic agents may be desirable, such as chemotherapeutic agents, immunosuppressive agents, cytokines, cytotoxic agents, nucleolytic compounds, radioactive isotopes, receptors, and pro-drug activating enzymes, which may be naturally occurring or produced by recombinant methods. The combined administration includes co-administration, using separate formulations or a single pharmaceutical formulation, and consecutive administration in either order, wherein preferably there is a time period while both (or all) active therapeutic agents simultaneously exert their biological activities.

In another embodiment, the other therapeutic agent comprises a cytokine. The term "cytokine" is a generic term for proteins released by one cell population which act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet growth factor; transforming growth factors (TGFs) such as TGF-alpha and TGF-beta; insulin-like growth factor-I and -II; erythropoietin (EPO); osteoinductive factors; interferons such as interferon-alpha, -beta and -gamma; colony stimulating factors (CSFs) such as macrophage-CSF (M-CSF); granulocyte-macrophage-CSF (GM-CSF); and granulocyte-CSF (GCSF); interleukins (ILs) such as IL-1, IL-1a, IL-2, IL-3, IL-4, IL-5, IL-6, IL-7, IL-8, IL-9, IL-11, IL-12, IL-15; a tumor necrosis factor such as TNF-alpha or TNF-beta; and other polypeptide factors including LIF and kit ligand (KL). As used herein, the term cytokine includes proteins from natural sources or from recombinant cell culture and biologically active equivalents of the native sequence cytokines.

It should be understood that in addition to the ingredients, particularly mentioned above, the formulations of the present invention may include other agents conventional in the art having regard to the type of formulation in question, for example, those suitable for oral administration may include flavoring agents.

As used herein and in the appended claims, the singular forms "a," "an," and "the" include plural reference unless the context clearly indicates otherwise. Thus, for example, reference to a "compound" is a reference to one or more such compounds and includes equivalents thereof known to those skilled in the art, and so forth. Unless defined otherwise, all technical and scientific terms used herein have the same meaning as commonly understood to one of ordinary skill in the art to which this invention belongs.

All publications and patents mentioned herein are incorporated herein by reference for the purpose of describing and disclosing, for example, the constructs and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

It is to be understood that this invention is not limited to the particular formulations, process steps, and materials disclosed herein as such formulations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The above disclosure generally describes the present invention. A more complete understanding can be obtained by reference to the following examples. These examples are described solely for purposes of illustration and are not intended to limit the scope of the invention. Although specific terms have been employed herein, such terms are intended in a descriptive sense and not for purposes of limitations.

EXAMPLES

Example 1

Preparation and Use of S. Aureus Lysate

Strains of S. aureus bacteria were deposited with the Czech Collection of Microorganisms (CCM) and have been assigned accession numbers CCM 4992, CCM 4993, CCM 4994, CCM 4995, CCM 4996, CCM 4997, CCM 4998. The bacteriophage used were from the group deposited with the Deutsche Sammlung von Mikroorganismen und Zeilkulturen GmbH (DSM) and having accession numbers DSM 14614, DSM 14615, and DSM 14616.

The bacteria, stored as a lyophilized culture were streaked onto trypton agar or a similar nutrient agar medium. After 24-48 h incubation at 37° C., 50 ml trypton medium was inoculated with the bacteria grown on the agar plate. The inoculated medium was incubated at 37° C. for 18-20 h and the volume added to 500 ml medium and incubated for 1-2 h (based on OD measured at 600 nm). The phage stock was then added, and the mixture was allowed to sit at room temperature for 12-18 h. The resulting lysate was centrifuged for 1 h at 5,000 rpm, and filtered using filters with a pore size of 0.22 μm (micrometer). The mixture was tested for sterility using blood agar and phage titration using a 2-layer agar technique.

Example 2

Screening of Bacterial Strains

Bacterial strains are screened for the most common antigenic pattern using immunogenic methods such as fluorescent antibody identification, FACS selection, ELISA, Western blots, SDS gel electrophoresis or by other detection methods known to those skilled in the art. Generally, the antigenic pattern is measured by SDS gel electrophoresis. The components of the SPL (as used in the Examples, SPL is at least one bacteria deposited as described herein that is lysed by at least one bacteriophage deposited as described herein) were separated in a gel and silver-stained. The antigenic pattern was determined by the presence/absence of particular bands in the gel.

Cultures of the selected bacteria were then infected by the introduction of phage homologues. The combinations of phage and bacteria were screened for phage strains that resulted in quantitative lysis of bacteria in a given time and strains that exhibited the most common antigenic pattern through the above-mentioned methods. Combinations of bacterial and phage strains that exhibit reproducible results in lysis were selected. Combinations of one bacterial strain and different phages resulted in different antigenic combinations which can also be utilized. The selected bacterial and phage strains were preserved by lyophylization.

Example 3

Lyophilization

Phage are prepared by lysing the host bacteria resulting in $10^9$ to $10^{10}$ phage particules per ml. 0.5 ml of the phage containing bacterial lysate was placed in tubes to which 0.2 ml of skim milk has been added. The tubes were then covered with a sterile porous cover. The tubes were lyophilized using a cryodesiccator instrument such as 30P2 or EdwardsEF03 using primary desiccation for 4 h and secondary desiccation for 6 h. The tubes are then sealed.

Each batch of phage containing bacterial lysate was tested for viability by plating the contents of one tube on a layer of host bacteria and obtaining the titer from two-fold dilutions. The titer is compared to the starting titer prior to lyophilization.

Example 4

Stability Analysis

The stability of the lysate cultures was determined through stability assays which were repeated cultures and subcultures on plates and in liquid media. The stability studies were performed to select bacterial and phage strains that were most stable upon storage. The criteria measured by methods known to those skilled in the art were the measuring of antigenic pattern by SDS gel electrophoresis; and phage virulence, excluding strains that become resistant to the phages used for infection. The cultures were also checked for reproducibility of antigenic patterns of lysates. Standardized inoculum of bacterial cells by the phages resulted in a very reproducible process of lysis. The resulting lysate was quantitatively and qualitatively analyzed by SDS gel electrophoresis.

Example 5

Preparation of Immunomodulators

Biological assays (e.g. blastic transformation, major antigenic proteins detected by Western blots, immunomodulation, etc.) were used to identify biologically active substances in the resultant lysates. A blastic transformation of peripheral lymphocytes was measured using individual fractions from SPL fractionated by chromatographic techniques. Activation markers or thymidine incorporation was used in the assay. Active fractions (those stimulating/inhibiting activation of peripheral lymphocytes) were further fractionated and used for isolation of a desired immunomodulator. One or more of these substances were then purified from one or more of the resultant lysates and identified and combinations were formed having the desired activities. Two or more of the resultant lysates identified were mixed together to yield the final polyclonal immunomodulator.

Example 6

Treatment with S. Aureus Lysates

Patients receive a subcutaneous dose 0.05 cc-0.3 cc (5 cc bottle) of the filtrate, at 24.5 µg/ml, prepared as described in Example 5 into the antebrachium (forearm). The dose is dependent on the age, clinical and immunological status of the patient. In hypersensitive patients, the doses should be 0.02 cc-0.03 cc. This smaller dose is divided in half and applied into both antebrachiums, with the same amount administered at each repetition. Doses are administered every 3-5 days following the resolution of any prior local reaction. The doses are gradually increased in non-hypersensitive patients to 0.05 cc subcutaneously, according to individual reaction of the patient. In severe cases, the dose can be increased to 1.0 cc subcutaneous per dose. If the local reaction lasts longer then 4 days, the same dose should be repeated in the subsequent administration.

In pediatric applications, i.e. for children aged 3-10 years, the dosage is decreased by 50% from the above regime, or may be administered according to individualized reactions.

The length of the treatment is dependent on the clinical and immunological status of the patient. Generally the lysates are administered every 3-5 days for 3 months. This dosing regime can be repeated periodically as a booster.

In the case of milder infection or in pediatric indications the lysate may be administered as nasal drops. The dose is 4 drops in each nostril daily for four days and thereafter every other day. Different routes of administration may be combined.

Example 7

Stimulation of Metabolic Burst in Phagocytic Cells (Monocytes and Polymorphonuclear Leukocytes) in Human Blood In Vitro Samples of blood were collected and stored with heparin. The heparinized blood was used 2 h and 7 h after collection and the 100-microliter samples were incubated with SPL and other negative (no addition) and positive controls including a peptide, formyl-MetLeuPhe (FMLP) (physiological stimulator), phorbol-12-myristate-13-acetate (PMA; strong stimulator).

A bursatest kit (Orpegen Pharma) was used for detection of metabolic burst in monocytes and polymorphonuclear leukocytes, respectively. Cell sorter (FACStrak) was used to count number of positive cells and total cells.

TABLE 1

| Sample | Polymorphonuclear leukocytes (% of positive cells) | | Monocytes (% of positive cells) | |
|---|---|---|---|---|
| | 2-h sample | 7-h sample | 2-h sample | 7-h sample |
| Negative control | 9.7 | 19.4 | 13.9 | 18.1 |
| SPL | 38.2 | 61.7 | 31.3 | 40.2 |

TABLE 1-continued

| Sample | Polymorphonuclear leukocytes (% of positive cells) | | Monocytes (% of positive cells) | |
|---|---|---|---|---|
| | 2-h sample | 7-h sample | 2-h sample | 7-h sample |
| FMLP | 13.8 | 26.3 | 15.8 | 18.8 |
| PMA | 99.6 | 99.8 | 98.7 | 99.5 |

Staphyloccocal lysate (SPL) induced metabolic burst in both monocytes and polymorphonuclear leukocytes in blood samples treated 2 h and 7 h after collection. This treatment led to an increase of 2.5-3.2-fold in monocytes and 3.6-4.3-fold in polymorphonuclear leukocytes versus the control.

Example 8

Activation of Sub-Population of T Cells in Human Blood In Vitro

Heparinized blood was incubated for 6 h with SPL and other negative (no addition) and positive controls including a peptide formyl-MetLeuPhe (physiological stimulator), phorbol-12-myristate-13-acetate (PMA; strong stimulator), serum-opsonized *Escherichia coli* cells (*E. coli*-o) (gram-negative bacterium containing lipopolysaccharides), and phytohemaglutinin (PHA; T-cell stimulator). Using Fastimmune test and FACStrak with triple fluorescence, early activation (CD69+) and production of interpheron gamma (IFN-g) was measured in CD4+ T cells. Isotype controls were used to subtract background staining.

TABLE 2

| Sample | CD69+ (% of positive cells) | (CD69+) & (IFN-g+) (% of positive cells) | (IFN-g+) (% of positive cells) |
|---|---|---|---|
| Negative control | 0.56 | 0 | 0.02 |
| PMA | 76.04 | 3.09 | 0.04 |
| fMLP | 0.85 | 0 | 0 |
| PHA | 76.19 | 2.90 | 0.21 |
| *E. coli*-o | 10.12 | — | 0 |
| SPL-50 ul | 14.25 | 0.63 | 0.01 |
| SPL-100 ul | 17.11 | 0.86 | 0.01 |
| SPL-150 ul | 18.37 | 0.75 | 0.04 |

SPL induced earlier and greater activation (CD69+) of CD4+ T cells than fMLP or *E. coli*-o and the levels reached about 20% of those induced by mitogens PMA or PHA.
When cells producing IFN-gamma were counted in the CD69+ subpopulation of CD4+ T lymphocytes stimulated with SPL, the levels were 30% of those stimulated with mitogens PMA or PHA.
*E. coli*-stimulated or fMLP-stimulated CD4+ T lymphocytes did not show any significant production of IFN-g in the CD-69+ sub-population. In contrast, SPL-stimulated cells showed significant production of IFN-gamma in the early-activated (CD69+) cells.

Example 9

Immunogenicity of Staphylolysate and its Components in a Rat Model
Materials and Methods
Animals The study was conducted using Wistar rats (weight 140-160 g); from Charles Rivers company (Charles River Laboratories, Inc., Wilmington, Mass. 01887-1000, U.S.A.). The rats were distributed by the AnLab, Inc (Anlab, Inc. Vídenská 1083, Prague 4, Czech Republic). The animals were held in experimental stables at the Institute of the Experimental Veterinary Medicine (IEVM), Bmo, Czech Republic (accreditation # 43322/2001-1020). The entire experiment was conducted in the stables with a protective barrier and monitored environment (light and temperature). Cage sizes and design were according to the Law of Czech Republic # 207/2004 regarding the protection, holding, and use of the experimental animals. The animals were checked daily by Veterinary Assistants and Veterinary Physician. There were no obvious changes of health status of the experimental or control animals during the experiment. For the purpose of the experiment, the animals were divided into 9 groups according to characteristics of the antigens which were used for the vaccination.

Isolation of Immunodominant Proteins

The immunomodominant proteins were selected based on the results of an experiment with rabbits vaccinated by the whole staphylolysate (SPL). At that time, the immunonodominant proteins were identified by the western blot (WB) method. The antigens were identified according to their apparent molecular weight (in kDa) as: 70 kDa, 50 kDa, 42 kDa, 36 kDa, 30 kDa, 30+<30 kDa, <30 kDa. See FIG. 1, which is a silver-stained, 10% SDS gel of each antigen fraction (lanes 1-7), an unfractionated SPL (full) and molecular size markers (far right lane).

The proteins were isolated from concentrated SPL (made by bacteriophage lytic infection of bacteria deposited as identified herein and by bacteriophage deposited as identified herein, (CCCM 4992 and CCM 4993 and 14614 phage) by SDS-PAGE method (Prep Cell Model 491; Bio-Rad, Hercules, Calif. 94547, U.S.A.). Four hundred ml of SPL was concentrated by ultrafiltration (Amicon, Bedford, Mass. 01730, U.S.A.), using 10-kDa-cut-off membrane (Omega, Pall Corporation, East Hills, N.Y. 11548, U.S.A.) to the final protein concentration 14 mg/ml (BCA Protein Assay Kit, Pierce, Rockford, Ill. 61105, U.S.A.). Consequently, the sample was concentrated 43-fold.

Two ml of the concentrated sample were mixed with 1 ml of SDS-PAGE reducing buffer (2:1), boiled for 5 min, and applied on the gel surface (85 mm×37 mm; first 10 mm was 5% focusing gel, the remainder was 8.5% separation gel) and separated using 25 mM Tris-192 mM glycine buffer (pH 8.3) with 0.1% SDS. The same buffer was used as elution buffer with a flow rate of 0.33 ml/min. Samples were collected during the 12 h separation using constant power 12 W. A fraction collector was used to collect the eluted proteins in fractions of 2.5 ml each. The resultant fractions were analyzed by SDS-PAGE and western blotting using immune rabbit sera to whole SPL lysate.

The fractions containing the most active proteins were dialyzed together against PBS for three days at 4° C. PBS buffer was changed daily. The fractions were then centrifuged (10,000 rpm for 15 min). The resulting supernatant was concentrated to 1 ml by ultrafiltration as described above and resuspended.

Challenge Test

The amounts of 0.2 ml of a 24.5 µg/ml solution of the identified, isolated proteins (shown in FIG. 1) were applied by subcutaneous injection into the back area of the animals. The same amount of antigen and the same area were used three weeks after the first vaccination for re-vaccination. The applied dose was a combination of 0.15 ml of the protein tested and 0.05 ml of the adjuvant. Al(OH)$_3$ was used as an adjuvant. The animals were divided into nine groups. Each of the groups contained three animals. Each group (seven groups) was vaccinated with one each of the seven different proteins previously separated by SDS-PAGE. (Shown in FIG. 1) The whole SPL was used for the eighth group. The ninth group was used as a negative control. Saline solution combined with the adjuvant was used for negative control.

Forty-eight days after vaccination the animals were challenged by scarifying and infecting with a wild-strain staphylococcus isolated from a clinical setting. On the left side, a 4 cm area was shaved. A two-prong needle was used to scarify by 3 vertical marks and 3 horizontal marks. A 0.2 cc suspension of the wild-type staphylococcal culture was applied to the scarified site with a rubber spatula. At 3 and 7 days post-infection, the infected sites were examined and the skin thickness was measured using skin calipers. The animals were sacrificed and examined histologically. Results are shown in Table 3. Percentages are compared to control animal that was not vaccinated prior to scarification and infection.

TABLE 3

Challenge test

| Antigen | 3 day (% change) | 7 day (% change) |
|---|---|---|
| 70 kDa | 120 | 120 |
| 50 kDa | 60 | 60 |
| 42 kDa | 200 | 100 |
| 36 kDa | 240 | 200 |
| 30 kDa | 0 | 120 |
| 30 + <30 kDa | 160 | 30 |
| <30 kDa | 60 | 30 |
| Whole SPL | 20 | 20 |
| Adjuvant only | 100 | 100 |

Antigens of 70 kDa, 50 kDa, 36 kDa, and 30 kDa were used in further tests to identify the proteins.

Specific Protein Fraction Antibody

The amounts of 0.2 ml (24.5 μg/ml solution) of the selected and tested proteins were applied by subcutaneous injection into the back area of the animals. The same amount and the same area were used three weeks after the first vaccination for re-vaccination. The applied dose was a combination of 0.15 ml of the protein tested and 0.05 ml of the adjuvant. $Al(OH)_3$ was used as an adjuvant. The animals were divided into nine groups. Each of the groups contained three animals. Each of the seven groups were vaccinated with one each of seven different proteins previously separated by SDS-PAGE. (Shown in FIG. 1) The whole SPL was used for the eighth group. The last group was used as a negative control. Saline solution combined with the adjuvant was used for negative control.

The blood samples were drawn two weeks after the first vaccination and one and two weeks after re-vaccination. During the procedure, the animals were fully anesthetized and the blood sample was drawn under the sterile conditions from vena cava cranialis. The amount of one ml of the blood was drawn. There was no anticoagulant present in the system of the tested animals at the time of the experiment.

Western Blot

Whole SPL was separated by SDS-PAGE method as described above and transferred onto nitrocellulose membranes (0.2 um pores; Schleicher&Schuell, Dassel, Germany). The membranes were than incubated with 100-fold diluted sera for one hour at room temperature. The specific antibodies were visualized using goat antibodies against rat IgG. The antibody was conjugated with horseradish peroxidase (Bethyl Laboratories, Inc., Montgomery, Tex.) and used at 3,000-fold dilution. Diamobenzidine (DAB) was used as a substrate.

A strong antibody response after the first vaccinations was seen in animals vaccinated with the proteins with molecular weight of 70 and 50 kDa. The same response was seen in the groups of the animals vaccinated with the whole SPL One week after the re-vaccination, the response was stronger. At that time (one week after the re-vaccination) the response to the proteins with molecular weight of 36 and 30 kDa was also detected. The response to the proteins with a molecular weight of 42 kDa and 30 kDa was not detected even two weeks after re-vaccination.

Identification of Specific Proteins Isolated From SPL

Figure 2:
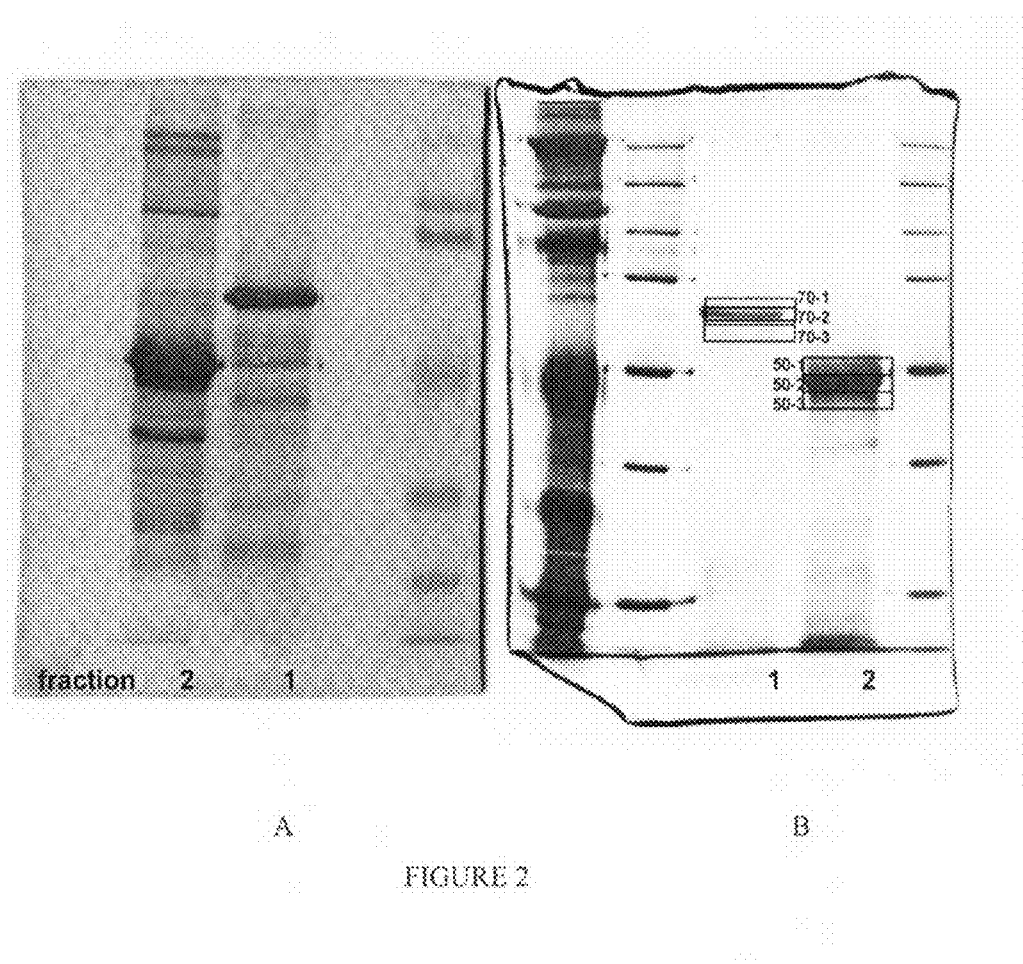
FIG. 2A is a Western blot of antigenic proteins of particular fractions from a staphylococcal lysate; B is a silver stained gel of the same fractions.
Figure 3:
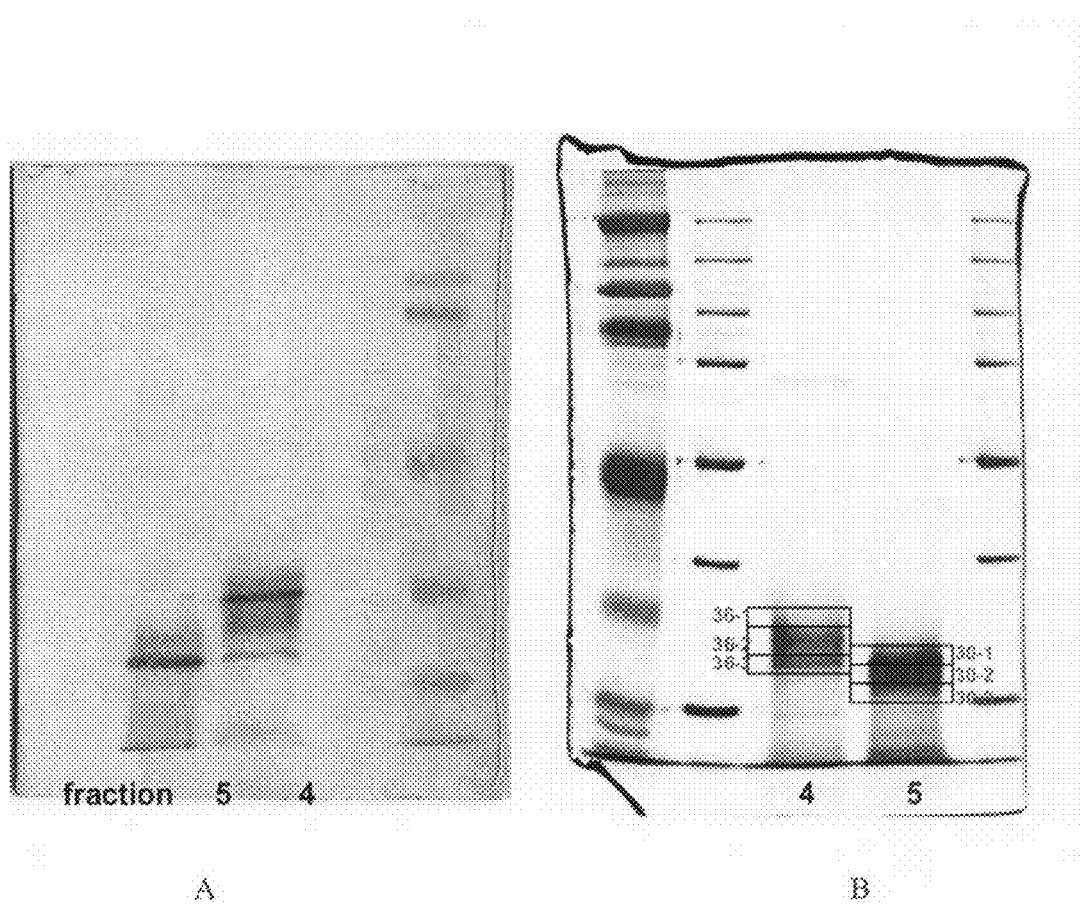
FIG. 3A is a Western blot of antigenic proteins of particular fractions from a staphylococcal lysate; B is a silver stained gel of the same fractions.

As shown in FIG. 2, A is a Western blot of Fractions 1 and 2 from FIG. 1 and B is a silver stain of the same gel. In FIG. 3, A is a Western blot of Fractions 4 and 5 from FIG. 1 and B is a silver stain of the same gel. The indicated fractions (boxed areas) were subjected to in-gel digestion by trypsin, at 40° C. for 2 hours. MALDI (Matrix Assisted Laser Desorption Ionization, Time-of-Flight mass spectrometry) was performed on each fraction, followed by LC-MS/MS to confirm data by sequencing. MASCOT database was searched for identification of the sequences found. FIG. 4 is a compilation of the proteins isolated and identified from SPL made from the lytic infection of the bacteria deposited as described herein, by the bacteriophage deposited and described herein (e.g. bacterial lysate of CCM 4992 and CCM 4993 by phage 14614). Fraction 1, the 70 kDa protein is a major tail sheath protein (phage protein), and the 50 kDa fraction is a phage capsid protein and a S. aureus enolase enzyme. Fraction 4 is fructose-bisphosphate aldolase of S. aureus, phage proteins, putative transport system binding lipoprotein, elongation factors Ts, phosphoenolpyruvate-protein phosphatase, ABC transporter (periplasmic amino acid-binding protein), and phage proteins ORF 45, ORF 57, ORF 95, capsid protein fragments, and putative bacteriophage baseplate protein. Fraction 5, 30 kDa, includes the 30S ribosomal protein S2, the 50S ribosomal protein L1, ABC transporter, and triosephosphate isomerase from S. aureus, and phage proteins ORF 95 and ORF 55.

What is claimed is:

1. A method of treating pathological conditions resulting from a *Staphylococcus aureus* (*S. aureus*) infection in humans or animals, comprising, administering to a human or animal having said pathological condition, a composition comprising at least one phage capsid protein isolated from a bacterial lysate derived from the infection of at least one bacterial strain of *S. aureus*, deposited with the Czech Collection of Microorganisms (CCM) under accession number CCM 4992 with at least one bacteriophage deposited with the Deutsche Sammlung von Mikroorganismen and Zellkulturen GmBH (DSM) having accession number DSM 14614, DSM 14615, or DSM 14616 and wherein the phage capsid protein has a molecular weight of 50 kDa.

2. The method of claim 1, wherein the composition is administered subcutaneously, intradermally, intramuscularly, nasally, or parenterally.

3. The method of claim 1, wherein the pathological condition is chronic upper respiratory disease, mastitis, wound infection, osteomyelitis, endocarditis, skin polymicrobial infections, bronchial asthma, chronic sinusitis, cystic fibrosis or acne vulgaris.

4. The method of claim 1, further comprising a bacterial lysate derived from at least one bacterial strain deposited with the CCM under accession number CCM 4992, CCM 4993, CCM 4994, CCM 4995, CCM 4996, CCM 4997, or CCM 4998.

5. The method of claim 1, further comprising one or more antigenic protein that is a phage major tail sheath protein, a *S. aureus* enolase enzyme, fructose-bisphosphate aldolase of *S. aureus*, *S. aureus* phosphoenolpyruvate-protein, *S. aureus* putative transport system binding lipoprotein, *S. aureus* elongation factor Ts, phage proteins ORF 45, ORF 57, ORF 95, and phage putative bacteriophage baseplate protein, *S. aureus* 30S ribosomal protein S2, *S. aureus* 50S ribosomal protein L1, *S. aureus* ABC (periplasmic amino acid-binding protein) transporter, *S. aureus* triosephosphate isomerase, or phage proteins ORF 95 or ORF 55, or combinations thereof.

6. A method of preventing a *Staphylococcus aureus* (*S. aureus*) infection or pathological conditions resulting from said *S. aureus* infection comprising administering to a human or animal a composition comprising at least one phage capsid protein isolated from a bacterial lysate derived from the infection of at least one bacterial strain of *S. aureus* deposited with the Czech Collection of Microorganisms (CCM) under accession number CCM 4992 with a bacteriophage deposited with the Deutsche Sammlung von Mikroorganismen and Zellkulturen GmBH (DSM) having accession number DSM 14614, DSM 14615, or DSM 14616 and wherein the phage capsid protein has a molecular weight of 50 kDa.

7. The method of claim 6, further comprising a lysate derived from a *S. aureus* bacterial strain deposited with the CCM under accession number CCM 4992, CCM 4993, CCM 4994, CCM 4995, CCM 4996, CCM 4997, or CCM 4998.

8. The method of claim 6, wherein the composition is administered subcutaneously, intradermally, intramuscularly, nasally, or parenterally.

9. The method of claim 6, further comprising one or more antigenic protein that is a phage major tail sheath protein, a *S. aureus* enolase enzyme, fructosebisphosphate aldolase of *S. aureus*, *S. aureus* phosphoenolpyruvate-protein, *S. aureus* putative transport system binding lipoprotein, *S. aureus* elongation factor Ts, phage proteins ORF 45, ORF 57, ORF 95, and phage putative bacteriophage baseplate protein, *S. aureus* 30S ribosomal protein S2, *S. aureus* 50S ribosomal protein L1, *S. aureus* ABC (periplasmic amino acid-binding protein) transporter, *S. aureus* triosephosphate isomerase, or phage proteins ORF 95 or ORF 55, or combinations thereof.

* * * * *